United States Patent
Batchelor et al.

(10) Patent No.: US 7,282,342 B2
(45) Date of Patent: Oct. 16, 2007

(54) METHODS FOR DETECTING WEAKLY IMMUNOGENIC ANALYTES

(75) Inventors: David Charles Batchelor, Auckland (NZ); Gregory Brian Thomas, Perth (AU); Bernhard Hermann Heinrich Breier, Auckland (NZ)

(73) Assignee: Neuren Pharmaceuticals Ltd., Auckland (NZ)

( * ) Notice: Subject to any disclaimer, the term of this patent is extended or adjusted under 35 U.S.C. 154(b) by 0 days.

(21) Appl. No.: 11/591,302

(22) Filed: Oct. 31, 2006

(65) Prior Publication Data

US 2007/0128660 A1    Jun. 7, 2007

Related U.S. Application Data

(63) Continuation of application No. 10/100,515, filed on Mar. 14, 2002, now abandoned.

(60) Provisional application No. 60/276,796, filed on Mar. 16, 2001, now abandoned.

(51) Int. Cl.
*G01N 33/53* (2006.01)
*G01N 33/563* (2006.01)
*G07K 16/00* (2006.01)

(52) U.S. Cl. .................. 435/7.1; 424/9.1; 424/130.1; 424/178.1; 530/387.1; 436/512; 436/514; 436/540

(58) Field of Classification Search .............. 435/7.1; 424/9.1, 130.1, 178.1; 530/387.1; 436/512, 436/514, 540
See application file for complete search history.

(56) References Cited

U.S. PATENT DOCUMENTS

| | | | |
|---|---|---|---|
| 4,444,879 A | 4/1984 | Foster et al. | |
| 4,816,567 A | 3/1989 | Cabilly et al. | |
| 6,187,906 B1 | 2/2001 | Gluckman et al. | |
| 2002/0151522 A1 | 10/2002 | Alexi | |
| 2003/0027760 A1 | 2/2003 | Gluckman et al. | |

FOREIGN PATENT DOCUMENTS

| EP | 0366 638 A2 | 5/1990 |
|---|---|---|
| WO | WO 95/17204 A1 | 6/1995 |
| WO | WO 98/14202 A1 | 4/1998 |
| WO | WO 99/65509 A1 | 12/1999 |

OTHER PUBLICATIONS

Tooyama et al., Production and immunohistochemical application of antiserum against Tyr-D-Ala-Phe, a N-terminal tripeptide common to dermorphin/deltorphin family. Peptides, 21, 2000, pp. 1649-1655.
Brennan, et al., "Chondroitin/Dematan Sulfate Proteoglycan in Human Fetal Membranes." The Journal of Biological Chemistry, Nov. 25, 1984, 259 (22), pp. 13742-13750.
Millan et al., "Seminoma-derived Nagao isozyme is encoded by germ-cell alkaline phosphatease gene." Proc. Natl. Acad. Sci. USA, vol. 85, May 1988, pp. 3024-3028.
Ballard, F. J. et al., "DS(1-3) IGF-I: A Truncated Form of Insulin-Like Growth Factor-I." International Journal of Biochemistry and Cell Biology, Exeter, GB, vol. 28, No. 10, 1996, pp. 1085-1087, XP002952721 ISSN: 1357-2725.
Saura, J. et al., "Neuroprotective Effects of Gly-Pro-Glu, the N-terminal tripeptide of IGF-1, in the hippocampus in vitro." Neuroreport. 1999, vol. 10, pp. 161-164, esp. p. 162, results.
Nilsson-Hakansson, et al. "Effects of IGF-1, truncated IGF-1 and the tripeptide Gly-Pro-Glu on acetylcholine release from parietal cortex of rat brain." Neuroreport. Aug. 6, 1993, vol. 4, No. 9, pp. 1111-1114.
Gelboin, H., "Cytochrome P450 and Monoclonal Antibodies." Pharmacological Reviews. 1993, vol. 45, No. 4, pp. 413-453, see entire document.
Vicki R. Sara, et al., "Identification of GLY-PRO-GLU (GPE), The Aminoterminal Tripeptide of Insulin-Like Growth Factor I Which Is Truncated In Brain, As A Novel Neuroactive Peptide." Biochemical and Biophysical Research Communications, vol. 165, No. 2, Dec. 15, 1989, pp. 766-771.
Jose Luis Millan, et al., "Seminoma-Derived Nagao Isozyme Is Encoded by a Germ-Cell Alkaline Phosphatase Gene," Proc. National Academy of Science USA, Developmental Biology, vol. 85, May 1988, pp. 3024-3028.

*Primary Examiner*—Long V. Le
*Assistant Examiner*—Lisa V Cook
(74) *Attorney, Agent, or Firm*—Borson Law Group, PC; D. Benjamin Borson

(57) ABSTRACT

GPE antibodies recognize GPE with high specificity. When used in a radioimmunoassay, they reliably measure the concentration of GPE. They may be used to extend the half-life of GPE both in vivo and in vitro, and in methods of purifying the GPE receptor. Two methods of rpHPLC accurately revolve GPE on the basis of its hydrophobicity.

15 Claims, 4 Drawing Sheets

METHODS FOR DETECTING WEAKLY IMMUNOGENIC ANALYTES

CROSS-REFERENCE TO RELATED APPLICATION

Claim of Priority

This application is a Continuation of Application Ser. No. 10/100,515, filed Mar. 14, 2002 now abandoned, which claims priority under 35 USC 119(e) of U.S. Provisional Appln. No. 60/276,796, filed Mar. 16, 2001, now abandoned, both of which are incorporated by reference into this application.

FIELD OF THE INVENTION

This invention relates to anti-GPE antibodies and their uses, and to analytical methods for GPE.

BACKGROUND TO THE INVENTION

GPE is the tripeptide glycyl-L-prolyl-L-glutamic acid (gly-pro-glu). It and the dipeptides glycyl-L-proline (gly-pro, GP) and L-prolyl-L-glutamic acid (pro-glu, PE) were first disclosed in EP 366638, which disclosed that GPE is effective as a neuromodulator and is able to affect the electrical properties of neurons.

The applicants have established that GPE has neuroprotective properties and that it therefore has utility in the prevention or inhibition of neuronal and glial cell death (WO 95/172904).

It would be desirable to have antibodies to GPE, both for an accurate method for the detection of GPE, and for therapeutic uses. It would also be desirable to have an accurate analytical method for GPE.

SUMMARY OF THE INVENTION

In a first aspect, this invention is antibodies against GPE ("anti-GPE antibodies").

In a second aspect, this invention is radioimmunoassay methods for the measurement of GPE using the anti-GPE antibodies of the first aspect of this invention, and kits for the same.

In a third aspect, this invention is methods of reverse phase high-performance liquid chromatography ("rpHPLC") that accurately resolves GPE and related compounds, and kits for the same.

In a fourth aspect, this invention is therapeutic methods for using the anti-GPE antibodies of the first aspect of this invention.

In a fifth aspect, this invention is a method of isolating and purifying the GPE receptor using the anti-GPE antibodies of the first aspect of this invention.

DESCRIPTION OF THE INVENTION

Figure 1:
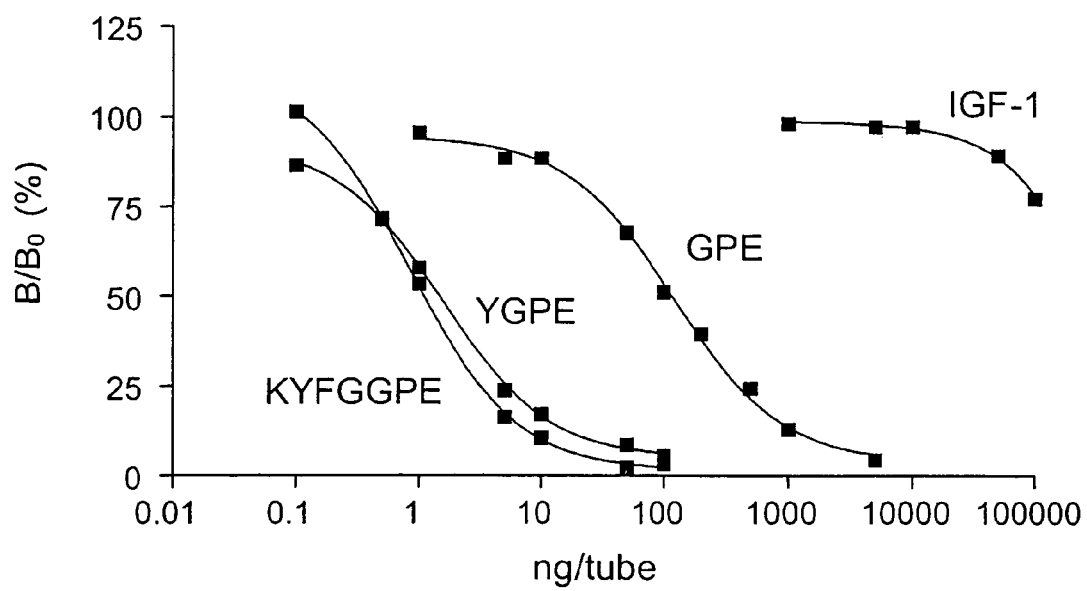
FIG. 1 is a radioimmunoassay displacement curve showing competitive displacement by unlabeled GPE of $^{125}$I-labeled YGPE binding to the CK5 antibody.

In a first aspect, this invention is antibodies against GPE ("anti-GPE antibodies"). These anti-GPE antibodies may be prepared by immunization of animals (e.g. rabbits) with immunogens containing GPE conjugated to an antigen such as keyhole limpet hemocyanin, as described in Examples 1, 2, and 6 below. The polyclonal anti-GPE antibody, which we refer to as CK5 antibody, specifically recognizes GPE and binds to GPE with high titer. In preferred embodiments of the invention, the antibodies to GPE are characterized by the ability to specifically bind to GPE using $^{125}$I-YGPE tracer with a final titer of at least about 1:600. In embodiments of the invention, the anti-GPE antibodies have the ability to bind specifically to GPE in normal tissues; or have the ability to bind specifically to GPE in diseased or injured tissue. In a most preferred embodiment of the invention, the anti-GPE antibodies have the ability to bind GPE in diseased or injured tissue of the central or peripheral nervous system. In another embodiment of the invention, the anti-GPE antibodies have the ability to specifically bind to Bolton and Hunter derivatized GPE using $^{125}$I-Bolton and Hunter derivatized GPE tracer with a final titer of at least about 1:18,000.

Anti-GPE antibodies find use in determining the pharmacokinetics and pharmacodynamics of GPE and GPE-related compounds (GPE analogs); and in assays to determine the neuroprotective concentration of GPE in blood and CSF required in the treatment of a disease or in the treatment of injury. In preferred embodiments of the invention, anti-GPE antibodies find use in assays to determine the neuroprotective concentration of GPE in blood and CSF required in the treatment of Parkinson's disease, multiple sclerosis, Alzheimer's disease, Huntington's disease, peripheral neuropathy, stroke, cardiac artery bypass graft surgery, ischemic brain injury, hypoxic brain injury, traumatic brain injury, and in the treatment of pancreatic disease including type 1 and type 2 diabetes. Further embodiments of the invention provide methods for the use of anti-GPE antibodies in the in vitro evaluation of GPE function. Such methods include evaluation of the effects of in vitro administration of GPE in the presence and in the absence of anti-GPE antibodies.

In a second aspect, this invention is a radioimmunoassay method for the measurement of GPE using the anti-GPE antibodies of the first aspect of this invention, as described in Example 3 below. The radioimmunoassay method allows for the selective quantitation of GPE in body fluids (e.g. blood, serum, cerebrospinal fluid, and urine) and in body tissues. The level of GPE may be a suitable marker of drug efficacy and/or effective dosing. In one embodiment of the invention, a radioimmunoassay kit comprises an anti-GPE antibody, a GPE standard, an assay buffer, a GPE compound (e.g. YGPE) for iodination, and a second antibody or a precipitated antibody, for example an antibody precipitated with polyethylene glycol (PEG). In another embodiment, the kit comprises an anti-GPE antibody, a GPE standard, an assay buffer, tritiated GPE, and a second antibody or a precipitated antibody. In a further embodiment, a radioimmunoassay kit comprises an anti-GPE antibody, a GPE standard, Bolton and Hunter reagent (N-succinimidyl-3-[4-hydroxyphenyl]propionate), a derivatizing buffer, an assay buffer, Bolton and Hunter derivatized GPE (BH-GPE) for iodination, and a second or precipitating antibody, for example an antibody precipitated with polyethylene glycol.

In a third aspect, this invention is methods of reverse phase high-performance liquid chromatography ("rpHPLC") that accurately resolves and quantitates GPE and related compounds. Two methods are described, in Examples 4 and 5, the first using derivatization of the amino groups with AccQTag® reagent, 6-aminoquinolyl-N-hydroxysuccinimidyl carbamate in acetonitrile and borate buffer, and the second, for the measurement of radioactive (e.g. tritiated) GPE, using a Hypercarb® column with no derivatization, and detection of the radioactivity in the eluate. The level of GPE may be a suitable marker of drug efficacy and/or effective dosing. In one embodiment, an rpHPLC assay kit comprises a GPE standard, 6-aminoquinolyl-N-hydroxysuccinimidyl carbamate and derivatizing buffer, a column, and column running buffer. In another embodiment, An rpHPLC assay kit comprises a radioactive GPE standard, a column, and column running buffer.

In a fourth aspect, this invention is therapeutic methods using the anti-GPE antibodies of the first aspect of this invention, as exemplified in Examples 7 and 8. This invention is methods for the extension of the half-life of GPE in vitro and in vivo comprising co-administration of GPE with anti-GPE antibodies-effective that a significant fraction of the GPE is bound to the anti-GPE antibody a significant fraction of the time, thereby protecting the GPE from degradation, non-specific binding, and metabolic modification and clearance. In further embodiments of the invention, antibodies to GPE may be used as non-blocking antibodies to modulate concentrations of GPE. In particular, antibodies to GPE may be used as non-blocking antibodies to modulate the free concentrations of GPE in vivo and in vitro.

In a fifth aspect, this invention is methods for the purification of the GPE receptor, comprising the use of the anti-GPE antibodies of the first aspect of this invention, as described in Example 9. In these methods, tissues, suspensions and solutions comprising GPE receptors contact surfaces, substrates, and solutions comprising GPE, effective to bind the GPE to the GPE receptors; and such surfaces, substrates, and solutions are subsequently contacted with anti-GPE antibodies so that the anti-GPE antibody binding to the GPE that is bound to GPE receptors is effective to aid in the purification of the GPE receptors.

The following non-limiting Examples illustrate this invention. All animal experimental protocols were conducted in accordance with guidelines approved by the University of Auckland Animal Ethics Committee.

EXAMPLE 1

Preparation of a Polyclonal Antibody to GPE (the CK5 Antibody), and Detection of GPE by the CK5 Antibody Three New Zealand White rabbits were injected subcutaneously with 200-300 µg of a peptide-conjugate immunogen (a 1:1 mixture of GPE conjugated to keyhole limpet hemocyanin (KLH) using glutaraldehyde (GA) and KYFG-GPE (SEQ ID NO:5) conjugated to KLH using GA) emulsified in Freund's complete adjuvant (primary immunization). Booster injections with the same immunogen emulsified in Freund's incomplete adjuvant were given at 3 to 4 weekly intervals. Blood samples were taken from the marginal ear vein 10 days after each injection for titer determination, and booster immunizations continued until a suitable titer was achieved (9 injections). The rabbits were then anesthetized and killed by terminal exsanguination. The blood was allowed to clot, then centrifuged, and the supernatant serum recovered. This serum contains the polyclonal anti-GPE antibody, which we refer to as CK5 antibody, and was frozen at −20° C. until ready for use. Since the presence of other non-GPE related immunologic reactions does not interfere with the reaction between GPE and its antibody (anti-GPE antiserum), the polyclonal CK5 antibody did not undergo any further purification. Characterization of the CK5 antibody was performed using both double antibody radioimmunoassay and immunohistochemical techniques.

The CK5 antibody was characterized using a standard double antibody radioimmunoassay technique. Tubes containing either 100 µL 0.02 M phosphate buffered saline assay buffer or peptide (GPE, YGPE (SEQ ID NO:4), KYFGGPE (SEQ ID NO:5), or IGF-1) dissolved in assay buffer at various concentrations were preincubated with CK5 antibody (diluted at 1:600) for 24 h at 4° C. $I^{125}$-labeled YGPE (10,000 cpm) was then added to the tubes. After a further 48 h incubation at 4° C., the bound and free GPE were separated by adding donkey anti-rabbit serum (1:100). The tubes were incubated with this second antibody overnight at 4° C. before centrifugation (3,200 rpm for 30 min), after which the supernatant was aspirated, and the precipitate counted in a gamma counter. The results are shown in FIG. 1. One antibody, CK5, was identified. Under the assay conditions described above, CK5 exhibits 14.7% specific binding to GPE at a final titer of 1:600, using $I^{125}$-labeled YGPE as the tracer. Unlabeled GPE was able to displace $I^{125}$-labeled YGPE with an $ED_{50}$ of approximately 200 ng/tube. Importantly, the CK5 antibody does not cross-react significantly with the GPE parent molecule, IGF-1.

The specificity of the CK5 antibody was further confirmed by Western blot and dot blot analysis. GPE immunoreactivity was detected when membranes were incubated with CK5 overnight at 4° C.; whereas preabsorption of CK5 overnight with excess unlabeled GPE completely abolished GPE immunoreactivity. Thus, CK5 is a specific antibody that recognizes and competitively binds GPE.

EXAMPLE 2

Detection of Bolton and Hunter Derivatized GPE Using the CK5 Antibody

Figure 2:
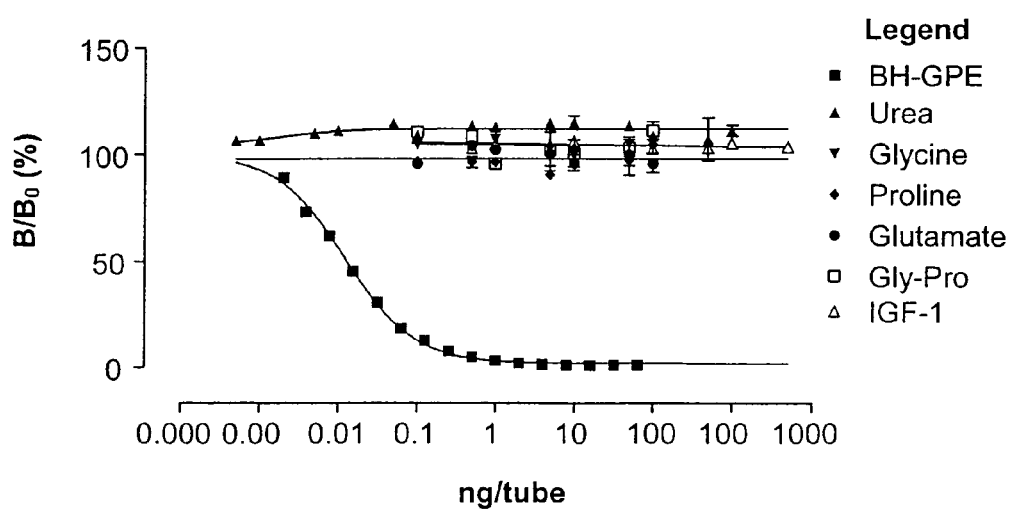
FIG. 2 is a radioimmunoassay displacement curve showing competitive displacement by unlabeled Bolton and Hunter derivatized GPE of $^{125}$I-labeled Bolton and Hunter derivatized YGPE binding to the CK5 antibody and lack of cross reactivity with the Bolton and Hunter derivatized forms of glycine, proline, glutamate, insulin-like growth factor-1 (IGF-1), gly-pro, and urea.
Figure 3:
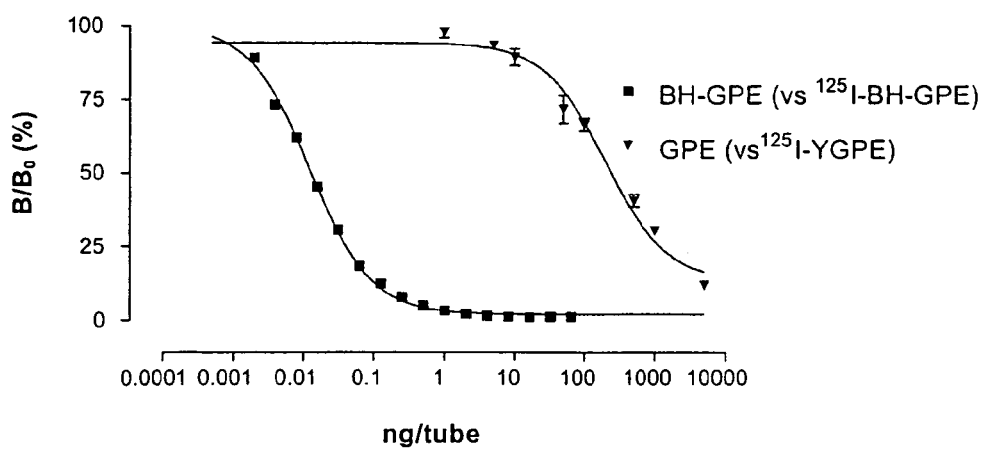
FIG. 3 compares the displacement of radio-labeled $^{125}$I-YGPE by GPE with the displacement of $^{125}$I-Bolton and Hunter derivatized GPE by Bolton and Hunter derivatized GPE.

The CK5 antibody was prepared as described in Example 1, and characterized using a modified double antibody radioimmunoassay technique. The CK5 antibody was used at a final dilution of 1:18,000. Tubes containing either 100

µL assay buffer (pH 7.8, 0.05M sodium phosphate), peptide (GPE, glycine, proline, glutamic acid, GP, PE, or IGF-1), or urea were derivatized with Bolton and Hunter reagent, N-succinimidyl-3-[4-hydroxyphenyl]propionate, and dissolved in assay buffer. The tubes were incubated with CK5 antibody and $I^{125}$-labeled Bolton and Hunter derivatized GPE (15,000 cpm) for 48 h at 4° C. The bound and free GPE were then separated by adding sheep anti-rabbit gamma globulin (1:100). The tubes were incubated with this second antibody for 4 h at room temperature before centrifugation (3,200 rpm for 45 min), after which the supernatant was tipped off and the precipitate counted in a gamma counter. The results are shown in FIGS. 2 and 3. Under the assay conditions described above, CK5 exhibits 50% specific binding to Bolton and Hunter derivatized GPE at a final titer of 1:18,000, using $I^{125}$ labeled Bolton and Hunter derivatized GPE as the tracer. Unlabeled Bolton and Hunter derivatized GPE was able to displace $I^{125}$ labeled Bolton and Hunter derivatized GPE with an $ED_{50}$ of approximately 0.01 ng/tube and the minimal detectable level of GPE was 0.005 ng/tube. The addition of either rat or human plasma to the standard curve resulted in parallel displacement. Importantly, CK5 antibody does not cross-react significantly with Bolton and Hunter derivatized glycine, proline, glutamic acid, GP, PE, IGF-1, or urea. The assay of differing volumes of rat plasma (25, 50, 75, 100 µL) containing known amounts of added GPE resulted in a linear relationship.

The specificity of CK5 was further confirmed by Western blot and dot blot analysis. GPE immunoreactivity was detected when membranes were incubated with CK5 overnight at 4° C.; whereas preabsorption of CK5 overnight with excess unlabeled GPE completely abolished GPE immunoreactivity. Thus CK5 is a specific antibody that recognizes and competitively binds Bolton and Hunter derivatized GPE with a higher $ED_{50}$ than for underivatized GPE. The $ED_{50}$ for modified displacement of Bolton and Hunter derivatized GPE was 0.0094 ng/tube (antibody diluted at a final dilution of 1/18,000), whereas the $ED_{50}$ for the standard displacement was 199.8 ng/tube (antibody diluted at a final dilution of 1/600).

EXAMPLE 3

Radioimmunoassay (RIA) Measurement of GPE in Biological Fluids and Tissues Using CK5 Antibodies and Bolton and Hunter Derivatized GPE This procedure uses a pre-RIA derivatization of the GPE-containing sample and comprises three steps: initial preparation of the sample using a tungstate extraction procedure to remove large proteins and to prevent overloading of the Bolton and Hunter reagent with an excess of amino groups; derivatization of samples and standards with Bolton and Hunter reagent; and a standard RIA protocol combining the CK5 antibody, $^{125}$I-labeled Bolton and Hunter derivatized GPE as the tracer, and PEG precipitation.

Part 1a: Acid Tungstate Precipitation from Blood, Cerebrospinal Fluid (CSF), and Urine Whole blood was collected into collection tubes containing a metalloprotease inhibitor, for example Sigma protease inhibitor cocktail, and centrifuged at 3,000×g for 15 min at 4° C. The supernatant (plasma) was transferred into a new tube and stored at −80° C. until ready for assay. CSF and urine were collected into collection tubes containing a metalloprotease inhibitor, for example Sigma protease inhibitor cocktail, and stored at −80° C. until ready for assay.

The samples were thawed on ice. During thawing of the samples, 800 µL of 0.04 M sulfuric acid was added to 1.5 mL micro-centrifuge tubes and incubated on ice. Aliquots (100 µL) of the samples were transferred to the micro-centrifuge tubes, and the tubes were vortexed and incubated on ice for 5 min, after which 100 µL of 10% sodium tungstate was added. The tubes were vortexed and incubated on ice for 10 min, twice. The tubes were then centrifuged at 20,000×g for 20 min at 4° C., after which 900 µL of the acid tungstate-treated sample was removed to a new micro-centrifuge tube and stored at −80° C. Tritiated GPE was used to determine a recovery level of 90-92% for the extraction procedure.

Part 1b: Acid Tungstate Precipitation from Tissue

All steps were performed on ice to prevent degradation of GPE. Approximately 50 mg of tissue was accurately weighed in a micro-centrifuge tube and 5 µL of protease inhibitor and 160 µL of 0.67 N $H_2SO_4$ added. The sample was homogenized for 3 min with a micro-centrifuge tube fitting pestle (approximately 100 strokes) or until a liquid homogenate was obtained. The pestle was rinsed into the tube with 400 µL of water using a pipette, and the tube sonicated for 1-5 sec. The probe was rinsed with 180 µL of water and the rinse added to the homogenate, then 60 µL of 10% sodium tungstate added, and the tube vortexed and incubated on ice for 10 min, twice. The tube was then centrifuged at 20,000×g for 20 min at 4° C. and the supernatant transferred to a new tube. To the pellet was added 100 µL of water, and the pellet was resuspended by vortexing and sonication for 1-5 sec, again rinsing the probe with 100 µL of water. The pellet was then centrifuged at 20,000×g for 20 min at 4° C., and the supernatant added to the original supernatant. Chloroform (100 µL) was added, and the tube was vortexed and centrifuged at 20,000×g for 5 min at 4° C. One mL of the upper layer was transferred to a new tube, taking care not to disturb the chloroform layer, and frozen at −80° C. Tritiated GPE was used to determine a recovery level of 92-94% for the extraction procedure.

Part 2: Bolton and Hunter Derivatization of Samples

To 100 µL of thawed treated sample was added 100 µL of 0.1 M phosphate buffer, and the mixture vortexed, after which 20 µL of 20 mM Bolton and Hunter reagent was added, and the samples incubated at room temperature for 4 h. The derivatized samples were then lyophilized overnight, re-suspended in 100 µL of assay buffer, and transferred to polypropylene plastic assay tubes (12×75 mm). For the standards, 1100 µL of Bolton and Hunter reagent was added to 1 mL of standard sub-stock containing 640 ng/mL phosphate buffer. The standard was incubated at room temperature for 4 h. The derivatized standards were lyophilized overnight, and re-suspended in 1 mL assay buffer.

Part 3: Radioimmunoassay of Bolton and Hunter Derivatized GPE

Rabbit CK5 antibody was used at a final dilution of 1:18,000 in assay buffer, and $^{125}$I-labeled Bolton and Hunter derivatized GPE (BH-GPE) was used as tracer at 150,000 cpm/mL in assay buffer. Sheep anti-rabbit gamma globulin (1% in 0.01 M PBS with 8% PEG), with 0.05% normal rabbit serum, incubated for 90 min at 4° C. before use, was the second antibody precipitation reagent.

Figure 4:
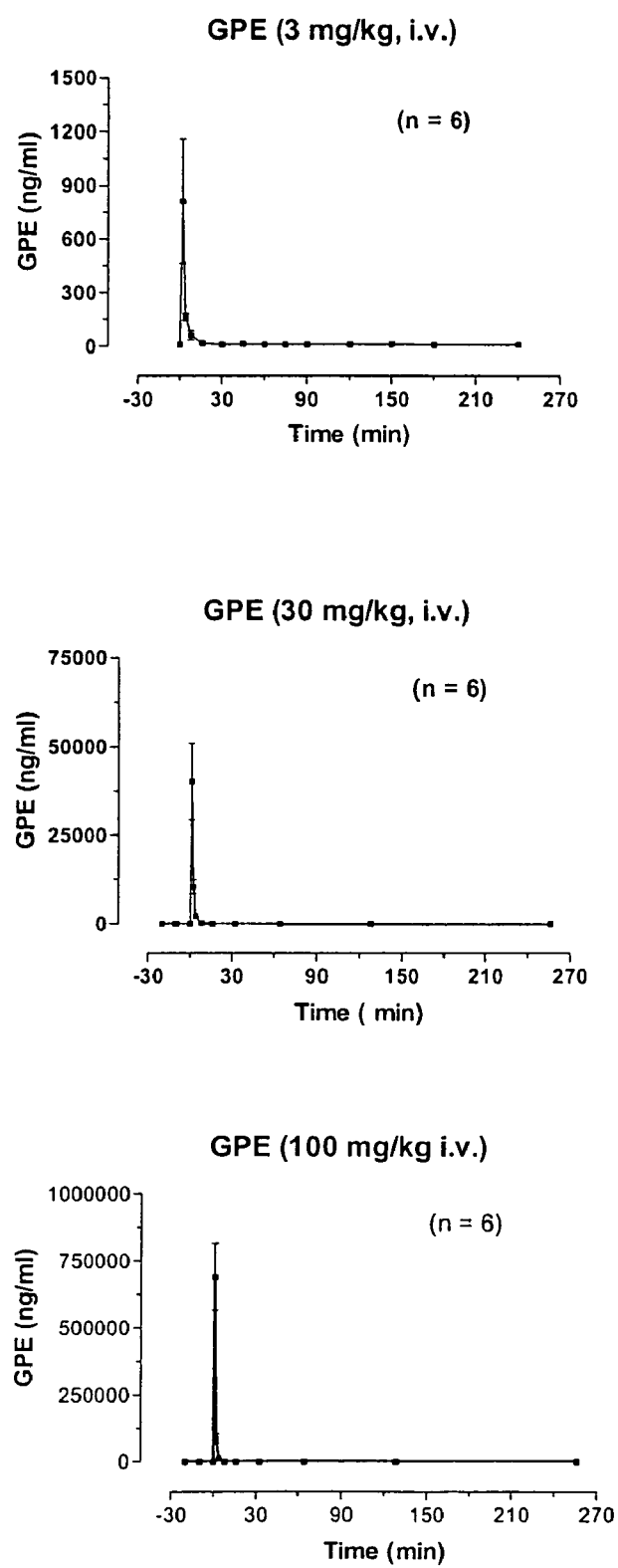
FIG. 4 shows the measurement of GPE in plasma using the CK5 antibody following intravenous administration of GPE at 3 mg/kg, 30 mg/kg and 100 mg/kg.

BH-GPE sub-stock containing 640 ng/mL BH-GPE was serially diluted to concentrations ranging from 640 ng/mL to 0.0002 ng/mL. Three 100 µL aliquots of each concentration were then transferred to polypropylene plastic assay tubes (12×75 mm). To each sample was added 100 µL antibody and 100 µL tracer, and the tubes vortexed. The samples were incubated for 72 h at 4° C., and 1 mL of secondary antibody reagent was added. The sample was incubated at room temperature for 2 h, then centrifuged at 3,000×g for 45 min at 4° C. The supernatant was poured off and counted for 1 min in a Cobra Gamma counter (Packard Biosciences). The results are shown in FIG. 4. The addition of the CK5 antibody and $^{125}$I-Bolton and Hunter derivatized GPE tracer in a radioimmunoassay allows the specific measurement of GPE plasma concentrations in samples following intravenous dosing. Using the CK5 antibody, GPE is detectable in blood following dosing and has a half-life of approximately 1-2 min.

EXAMPLE 4

Reverse Phase HPLC Using ACCQTAG® Derivatization

GPE-containing samples were prepared as in Parts 1a and 1b of Example 3. The samples were derivatized by the Waters AccQTag® method, which involves incubation of the sample with 10 mM 6-aminoquinolyl-N-hydroxysuccinimidyl carbamate in acetonitrile and borate buffer at 55° C. for 10 min and converts primary and secondary amino groups to fluorescent derivatives, before being transferred to the HPLC injection vial. These reaction products were resolved by HPLC and compared to known amino acid standards. The reverse phase HPLC system consisted of a Waters 2690 Alliance separation module, a 300×3.9 mm C18 Pico-tag (Waters) column at 37° C., and a Waters 474 fluorescence detector set at 250 nm excitation, 395 nm detection, gain 100. This was linked to a PC running the Waters Millennium$^{32}$ program (Waters Corporation, Milford Mass. 01757). The mobile phase consisted of three components: component A was MilliQ water, component B was a buffer made up with 80 mM sodium acetate, 3 mM triethylamine, 2.7 µM EDTA, brought to pH 6.43 with orthodontic acid, and component C was acetonitrile. The mobile phase was run in the gradient shown in Table 1 below over 112.1 min, at a flow rate of 1.2 mL/min at 37° C.

TABLE 1

| Time (min) | % A | % B | % C | Curve |
|---|---|---|---|---|
| 0 | 49.9 | 49.9 | 0.2 | 6 |
| 13 | 48.7 | 48.7 | 2.6 | 6 |
| 27 | 48.6 | 48.6 | 2.8 | 6 |
| 50 | 48.5 | 48.5 | 3 | 6 |
| 75 | 46 | 46 | 8 | 6 |
| 82 | 45 | 45 | 10 | 6 |
| 98 | 43 | 43 | 14 | 6 |
| 108 | 41.5 | 41.5 | 17 | 11 |
| 108.1 | 40 | 0 | 60 | 11 |
| 112.1 | 49.9 | 49.9 | 0.2 | |

Figure 5:
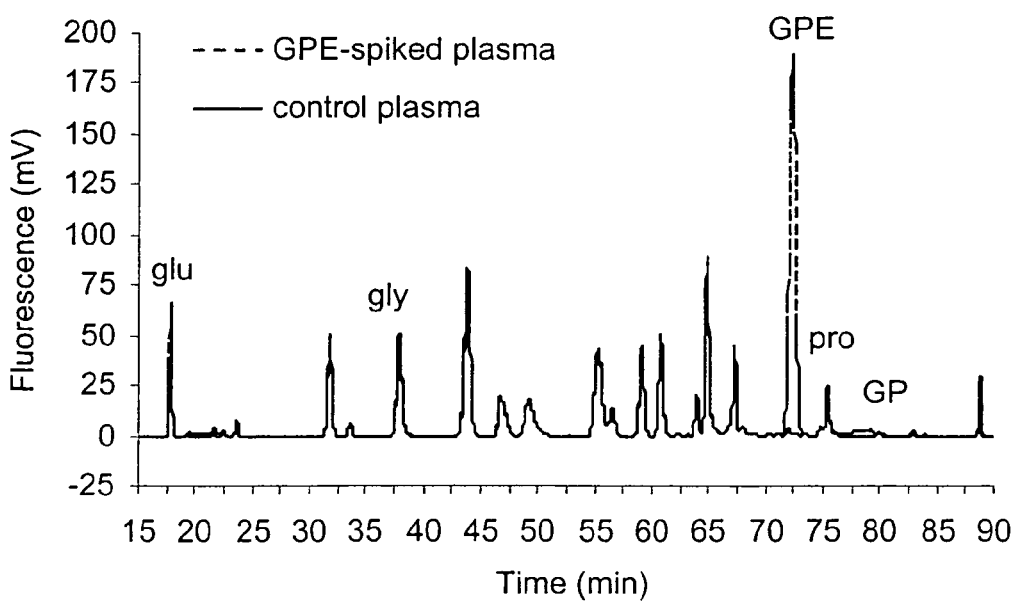
FIG. 5 is a rpHPLC chromatogram showing the resolution of GPE in plasma following derivatization by AccQTag® reagent.
Figure 6:
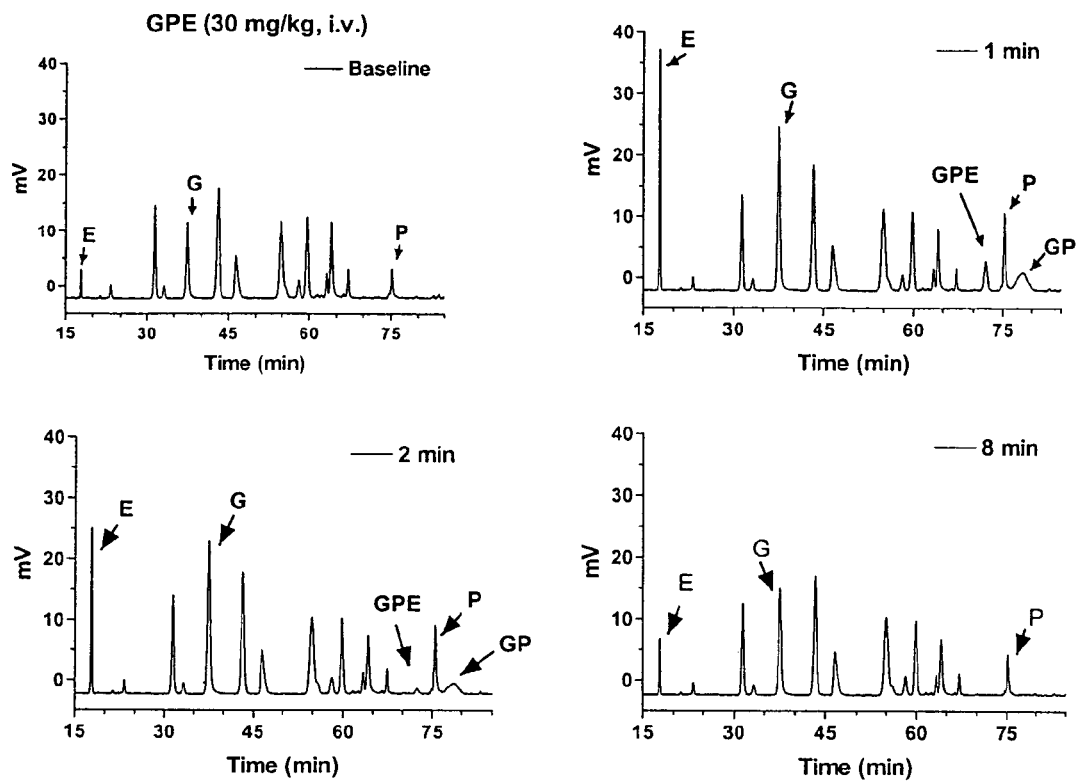
FIG. 6 is a rpHPLC chromatogram showing detection of GPE in blood at various times following intravenous administration of 30 mg/kg GPE.

The results are shown in FIGS. 5 and 6. The rpHPLC elution profile of FIG. 5 shows that GPE elutes with a retention time of approximately 72 min, and the GPE peak is sharp and resolved and clearly detectable above control plasma. No GPE was detected in 'unspiked' control plasma. This method has also been repeated with tritiated GPE, which eluted with the same retention time. The profiles of FIG. 6 show that rpHPLC allows the specific measurement of GPE plasma concentrations in samples at different times following intravenous dosing. Reverse phase HPLC of AccQTag derivatized GPE-containing samples is a reliable and sensitive method to detect GPE.

EXAMPLE 5

Reverse Phase HPLC Using a Hypercarb® Column

GPE-containing samples were prepared as in Parts 1a and 1b of Example 3. Samples were thawed on ice before being transferred to the HPLC injection vial. The reverse phase HPLC system consisted of a 100×4.6 mm Hypercarb 5 µm (Hypersil) column between a Waters Wisp Autosampler (Waters) and a BioCAD Sprint workstation (Applied Biosystems) running Version 2.062 of the BioCAD workstation software and an Advantec fraction collector set to collect 0.5 mL fractions. Samples were run onto the column in a mobile phase consisting of 10% methanol, 0.1% trifluoroacetic acid in MilliQ water, then eluted using a linear gradient with a mobile phase consisting of 90% methanol, 0.1% trifluoroacetic acid in MilliQ water using 0-100% gradient over 25 min as in Table 2 below, with a flow rate of 1.0 mL/min at room temperature. UV absorbance detection was set at 220 mm, and 0.5 mL fractions were collected into 5 mL scintillation vials from time of injection until the end of the gradient. Scintillation fluid (4 mL) was then added to each vial, and the samples counted in a 14XX Rack-beta scintillation counter (Wallac, Perkin Elmer).

TABLE 2

| Time (min) | 10% MeOH/ 0.1% TFA | 90% MeOH/ 0.1% TFA | Event |
|---|---|---|---|
| 0 | 100 | 0 | |
| 5 | 100 | 0 | |
| 10 | 100 | 0 | Injection/fraction start |
| 35 | 0 | 100 | Fraction collection stop |
| 40 | 0 | 100 | |
| 41 | 100 | 0 | |
| 45 | 100 | 0 | |

Figure 7:
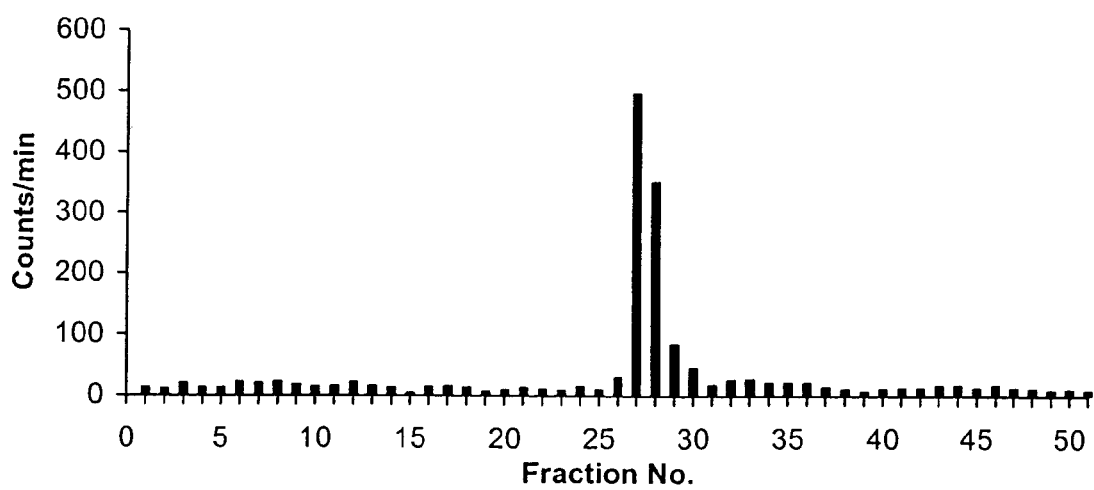
FIG. 7 is an rpHPLC chromatogram showing the resolution of tritiated GPE in plasma.

The results are shown in FIG. 7. Tritiated GPE eluted in fractions 27 and 28. The GPE peak is sharp, resolved, and clearly detectable. Metabolic products of tritiated GPE (Gly-Pro and Proline) elute in the void. The method was repeated with "cold" (non-tritiated) GPE and eluted with the same retention time.

EXAMPLE 6

Polyclonal Antibody Production in Rabbits

Twelve female New Zealand White rabbits are injected subcutaneously with 600-1000 µg of peptide-conjugate emulsified in Freund's complete adjuvant. Three rabbits received a mixture of 300 µg of GPE conjugated to KLH using GA and 300 µg KYFGGPE (SEQ ID NO:5) conjugated to KLH using GA; three rabbits received a mixture of 300 µg GPE conjugated to KLH using GA and 600 µg GPE conjugated to KLH using diethyl carbodiimide, and six rabbits, primed with Bacillus Calmette-Guerin [BCG] vaccine, received 1000 µg CGPE conjugated to a purified protein derivative of tuberculin (Statens Serum Institut, Denmark) using sulfosuccinimidyl 4-(N-maleimidomethyl) cyclohexane-1-carboxylate (sulfo-SMCC, Pierce, Ill., USA). Booster injections emulsified in Freund's complete adjuvant were given at 3-4 weekly intervals. Blood samples were taken from the marginal ear vein 10 days after each injection for titer determination, and regular immunizations continued for up to 8 months (maximum 10 injections) until a suitable titer was achieved.

Characterization of the anti-GPE antibody was performed using both the double antibody radioimmunoassay technique described in Examples 1 and 2 above and by immunocytochemistry.

EXAMPLE 7

Passive Immunization Against GPE in Rats

Following hypoxic-ischemic injury, rats were treated with either GPE alone or GPE combined with anti-GPE antibodies. Nine pairs of adult Wistar rats (280-320 g) were prepared under halothane/$O_2$ anesthesia. The right side carotid artery was ligated. To facilitate the intracerebroventricular administration of treatment, a guide cannula was placed on the dura at stereotaxic coordinates AP+7.5 mm, R+1.5 mm. The rats were allowed to recover for 1 h and were then placed in an incubator with humidity 90±5% and temperature 31±0.5° C. for 1 h before hypoxia. The oxygen concentration was then reduced and maintained at 6±0.2% for 10 min. The rats were kept in the incubator for 2 h after hypoxia and then treated with either 3 μg GPE or 3 μg GPE plus 25 μL anti-GPE antibodies. A further 6 rats were used as normal controls. The rats were killed by being deeply anaesthetized with an overdose of pentobarbital and then transcardially perfused with normal saline followed by 10% buffered formalin. The brains were removed and kept in the same fixative for two days before being processed using a standard paraffin tissue procedure.

Coronal (8 μm) sections were cut from the striatum, cerebral cortex and hippocampus, mounted on glass slides and stained with Thionin and Acid Fuchsin. With the experimenter blinded to the treatment groups, the histological outcome was assessed using two levels: at the mid-level of the striatum and the level where the ventral horn of the hippocampus just appears. Dead neurons are acidophilic (red), and have contracted nuclei. An indirect technique was used to determine the extent of cortical damage; the area of intact cortical tissue in both hemispheres was measured using an image analyzer (SigmaScan (SPSS Science) Chicago, Ill.). Brain tissue with selective neuronal death and/or pan-necrosis was considered to be damaged. The right/left (R/L) ratio of area of intact cortex was compared between the treatment groups. Surviving neurons from both sides of the CA1-2 subregions of the hippocampus were counted from the boundary between CA3 and CA1-2 and towards CA1-2 for 600 μm. The R/L ratio of surviving neurons in the CA1-2 subregions of the hippocampus was compared between treatment groups. Striatal damage was scored using the following scoring system: 0, no tissue damage; 1, <5% tissue damage; 2, <50% tissue damage; 3, >50% tissue damage. Passive immunization against GPE actively blocks the neuroprotective effects of GPE, suggesting that following GPE treatment, neuroprotective effects are specific to GPE action.

EXAMPLE 8

Passive Immunization Against GPE in Lesioned Rats

Following a lesion with 6-hydroxy dopanine (6-OHDA), rats were treated with GPE either alone or combined with anti-GPE antibodies. Eighteen male Wistar rats (50-60 days, 280-310 g) were used for the study. Under 3% halothane anesthesia, the 6-OHDA (8 μg in 2 μL 0.9% saline containing 1% ascorbic acid) was administered into the right medial forebrain bundle (MFB) at stereotaxic coordinates AP +4.7 mm, R+1.6 mm, V−8 mm using a 100 μL Hamilton syringe with a 30 G needle controlled by a microdialysis infusion pump at an infusion rate of 0.2 μL/minute. The infusion needle was slowly withdrawn 5 minutes after the infusion. The surgery and procedures for the intracerebroventricular administration are described in Guan et al. (1993), The effects of IGF-I treatment after hypoxic-ischemic brain injury in adult rats, *Journal of Cerebral Blood Flow and Metabolism* 13: 609-616. A 6 mm long, 21 G guide cannula is fixed on the top of the dura with coordinates of AP+7.5 mm, R+1.5 mm immediately after the injection of 6-OHDA. Either 3 μg GPE, 3 μg GPE plus 25 μL anti-GPE antibodies, or vehicle was infused into the right lateral ventricle 2 h after lesion at an infusion rate of 2 μL/min. Rats were then housed in a holding room with free access to food and water for the next two weeks. The rats were killed by being deeply anaesthetized with an overdose of pentobarbital and then transcardially perfused with normal saline followed by 10% buffered formalin. The brains were removed and kept in the same fixative for two days before being processed using a standard paraffin tissue procedure.

Coronal sections from the striatum and the substantia nigra compacta (SNc) were cut on a microtome to 8 μm thickness, mounted on chrome-alum coated slides, and air-dried. For staining, the sections were deparaffinized, rehydrated, washed with 0.1 M phosphate buffered saline (PBS), pretreated with 1% $H_2O_2$ for 20 min, washed with 0.1 M PBS (3×5 min), and incubated in rabbit polyclonal antisera raised against tyrosine hydroxylase (Protos Biotech, USA) diluted 1:500 with 1% goat serum for 48 h at 4° C. The sections were then washed in PBS (3×5 min) and incubated overnight at room temperature in donkey anti-rabbit biotinylated secondary antibody (1:200, Amersham Life Science). The sections were washed again in 0.1 M PBS, incubated in streptavidin-linked horse radish peroxidase (1:200, Amersham Life Science) for 3 h, washed again in PBS, and then treated with 0.05% 3,3'-diaminobenzidine tetrahydrochloride and 0.01% $H_2O_2$ to produce a brown reaction product. The sections were then dehydrated in a graded alcohol series, cleared in xylene, and coverslipped with mounting medium.

With the experimenter blinded to the treatment groups, the number of tyrosine hydroxylase-positive (TH-positive) neurons on both sides of the SNc are counted using light microscopic examination (20× magnification) at three representative levels (AP+4.2 mm, +3.8 mm and +3.4 mm). The average densities of TH staining on both sides of the SNc are measured using an image-analyser (Mocha image analysis software). The average density of TH staining in the striatum is also measured using three adjacent sections from the middle of the striatum. The average density from the background reading is also measured. The difference in average density between the background and TH staining is calculated and used for data analysis. Right/left (R/L) ratios of the number of TH-positive neurons and the R/L ratio of the average density of TH staining from each level of the SNc is compared between the two treatment groups using two-way ANOVA. The R/L ratio of the TH staining density from three striatal sections is averaged and compared between the two groups using the t-test. Data is presented as mean±SEM. The morphological changes in the SNc and the striatum are photographed using a Leitz Dialux light microscope (10× and 40× magnifications) or a digital camera and the images processed using Adobe Photoshop® and Pagemaker® software. Passive immunization against GPE actively blocks the neuroprotective effects of GPE, suggesting that following GPE treatment neuroprotective effects are specific to GPE action.

EXAMPLE 9

Purification of the GPE Receptor

CK5 antibody was resuspended to a final concentration of 1/100 in 0.1M PBS pH 7.8. Sulfosuccinimidyl 2-[m-azido-o-nitrobenzamido]-ethyl-1,3'-dithiopropionate (SAND) in DMSO was added to a final concentration of 10 mM, and the reaction mixture incubated in the dark at 37° C. for 30 min. Unreacted SAND was removed by dialysis against several changes of 0.1M PBS, pH 7.8. The CK5-SAND complex was then stored at −80° C. until used. Fresh frozen brain slices (60 μm thick) or cells grown in 80 cm cell culture dishes were briefly exposed to 100 μM GPE or vehicle in 0.1M PBS, excess unbound GPE was then washed off with three washes of PBS, and the samples incubated in the dark for 1 h with CK5-SAND complex to enable the antibody to bind to the GPE, which is bound to its receptor. Photoactivation by 3-5 bright camera flashes resulted in crosslinking of the CK5-SAND complex to the GPE receptor. The cells/tissues were then solubilized in 1% Triton in 25 mM HEPES, pH 7.6; and CK5-SAND-receptor immunocomplexes were then purified using a HiTrap Protein G Column (Amersham Pharmacia Biotech) following the manufacturer's instructions. 2-Mercaptoethanol was then added to the sample extract to cleave the crosslinker; and the separated CK5 antibody and GPE receptor were resolved by two dimensional electrophoresis before blotting to PVDF membranes and staining with Coomassie blue.

GPE and vehicle treated extractions were compared and potential receptor bands identified. These bands were excised and sequenced using a gas-phase Sequencer (model 470A, Applied Biosystems) following the manufacturer's instructions or by MS/MS analysis.

All documents cited throughout this application are incorporated by reference into this application. Those persons skilled in the art will appreciate that the present invention is described by way of example only and is not intended to be limited to the specific experimental details given. Numerous changes and variations can be made without departing from the scope of the invention, and all such changes and variations are intended to be within the scope of the following claims and their equivalents.

We claim:

1. A method for detecting Gly-Pro-Glu (GPE) in a sample; comprising:
   (a) providing an antibody raised against said GPE derivatized with a reagent selected from the group consisting of keyhole limpet hemocyanin (KLH), diethyl carbodiimide, 6-aminoquinolyl-N-hydroxysuccinimidyl carbamate, sulfosuccinimidyl 4-(N-maleimidomethyl) cyclohexane-1-carboxylate, sulfosuccinimidyl 2-[m-azido-o-nitrobenzamido]-ethyl-1,3'-dithiopropionate and N-succinimidyl-3-[4-hydroxyphenyl]propionate;
   (b) providing a sample containing an unknown amount of said GPE;
   (c) derivatizing said GPE in the sample of step (b) using the reagent selected in step (a);
   (d) permitting said derivatized GPE of step (c) to bind with said antibody of step (a); thereby producing a derivatized GPE-antibody complex; and
   (e) detecting said derivatized GPE-antibody complex.

2. The method of claim 1, wherein the antibody affinity for the GPE is 200 ng/tube.

3. The method of claim 1, wherein the antibody is a polyclonal antibody directed against a Bolton-Hunter (N-succinimidyl-3 -[4-hydroxyphenyl]propionate) derivatized GPE.

4. The method of claim 1, wherein the antibody is a monoclonal antibody directed against a Bolton-Hunter (N-succinimidyl-3-[4-hydroxyphenyl]propionate) derivatized GPE.

5. The method of claim 1, wherein the antibody has half maximal binding to an iodinated tracer analog of the GPE with a final titer of at least about 1:600.

6. The method of claim 1, wherein the antibody has half maximal binding to the derivatized GPE with a final titer of at least about 1:18,000.

7. The method of claim 1, wherein detection of said derivatized GPE antibody complex has an $ED_{50}$ of about 0.01 ng/tube.

8. The method of claim 1, wherein the $ED_{50}$ to displace the derivatized GPE antibody complex with derivatized GPE is about $10^4$ times greater than the $ED_{50}$ to displace the underivatized GPE antibody complex with underivatized GPE.

9. The method of claim 1, wherein the antibody does not substantially cross react with derivatized glycine, proline, glutamic acid, gly-pro (GP), pro-glu (PB), IGF-1 or urea.

10. The method of claim 1, wherein the GPE is derivatized with Bolton-Hunter reagent (N-succinimidyl-3-[4-hydroxyphenyl]propionate).

11. The method of claim 1, wherein the GPE is derivatized with 6-aminoquinolyl-N-hydroxysuccinimidyl carbamate.

12. The method of claim 1, further comprising:
   (f) eluting the derivatized GPE antibody complex in a chromatographic system;
   (g) exciting the derivatized GPE antibody complex at an appropriate UV absorbing wavelength; and
   (h) detecting the derivatized GPE antibody complex at an appropriate UV emitting wavelength.

13. The method of claim 11, further comprising:
   (f) eluting the derivatized GPE antibody complex in a chromatographic system;
   (g) exciting the derivatized analyte antibody complex at 250 nm wavelength; and
   (h) detecting the derivatized analyte antibody complex at 395 nm wavelength.

14. A method for determining the amount of unknown GPE comprising:
   (a) providing an antibody raised against said GPE derivatized with a reagent selected from the group consisting of KLH, glutaraldehyde, diethyl carbodiimide,6-aminoquinolyl-N-hydroxysuccinimidyl carbamate, sulfosuccinimidyl 4-(N-maleimidomethyl) cyclohexane-1- carboxylate, sulfosuccinimidyl 2-[m-azido-o-nitrobenzamido]-ethyl-1,3'-dithiopropionate and N-succinimidyl-3-[4-hydroxyphenyl]propionate;
(b) providing a sample containing an unknown amount of said GPE;
(c) derivatizing said GPE in the sample of step (b);
(d) permitting said derivatized GPE of step (c) to bind with said antibody of step (a); thereby producing a derivatized GPE-antibody complex;
(e) permitting said excess antibody of step (d) to incubate with a radioactive tracer derivatized analyte; thereby producing a radioactive tracer derivatized GPE-antibody complex;
(f) isolating the mixture of the derivatized GPE-antibody and radioactive tracer derivatized GPE-antibody complexes;
(g) eluting the said complexes in a chromatographic system; and
(h) analyzing the eluent and determining the amount of unknown GPE on the basis of the excess of antibody not bound to the derivatized GPE determined on the basis of emitted radioactivity of the tracer derivatized GPE antibody complex.

15. The method of claim 13, wherein a precipitating antibody is used in step (f) to isolate the mixture of the derivatized GPE-antibody and radioactive tracer derivatized GPE antibody complexes.

* * * * *

SEQUENCE LISTING

```
<160> NUMBER OF SEQ ID NOS: 6

<210> SEQ ID NO 1
<211> LENGTH: 3
<212> TYPE: PRT
<213> ORGANISM: Human

<400> SEQUENCE: 1

Gly Pro Glu
1

<210> SEQ ID NO 2
<211> LENGTH: 2
<212> TYPE: PRT
<213> ORGANISM: Artificial
<220> FEATURE:
<223> OTHER INFORMATION: GP fragment of GPE

<400> SEQUENCE: 2

Gly Pro
1

<210> SEQ ID NO 3
<211> LENGTH: 2
<212> TYPE: PRT
<213> ORGANISM: Artificial
<220> FEATURE:
<223> OTHER INFORMATION: PE fragment of GPE

<400> SEQUENCE: 3

Pro Glu
1

<210> SEQ ID NO 4
<211> LENGTH: 4
<212> TYPE: PRT
<213> ORGANISM: Artificial
<220> FEATURE:
<223> OTHER INFORMATION: Y + GPE
```

```
<400> SEQUENCE: 4

Tyr Gly Pro Glu
1

<210> SEQ ID NO 5
<211> LENGTH: 7
<212> TYPE: PRT
<213> ORGANISM: Artificial
<220> FEATURE:
<223> OTHER INFORMATION: keyhole limpet hemocyanin

<400> SEQUENCE: 5

Lys Tyr Phe Gly Gly Pro Glu
1               5

<210> SEQ ID NO 6
<211> LENGTH: 4
<212> TYPE: PRT
<213> ORGANISM: Artificial
<220> FEATURE:
<223> OTHER INFORMATION: C + GPE

<400> SEQUENCE: 6

Cys Gly Pro Glu
1
```